(12) United States Patent
Heidal et al.

(10) Patent No.: US 6,830,699 B2
(45) Date of Patent: Dec. 14, 2004

(54) PROCESS AND MEANS TO PREVENT MICROORGANISMS BLOOMING IN AN AQUATIC SYSTEM

(75) Inventors: Mikal Heidal, Bones (NO); Gunnar Bratbak, Ulset (NO)

(73) Assignee: Forinnova AS, Bergen (NO)

( * ) Notice: Subject to any disclaimer, the term of this patent is extended or adjusted under 35 U.S.C. 154(b) by 150 days.

(21) Appl. No.: 10/168,436

(22) PCT Filed: Jan. 4, 2001

(86) PCT No.: PCT/NO01/00004

§ 371 (c)(1),
(2), (4) Date: Aug. 19, 2002

(87) PCT Pub. No.: WO01/49614

PCT Pub. Date: Jul. 12, 2001

(65) Prior Publication Data

US 2003/0047518 A1 Mar. 13, 2003

(30) Foreign Application Priority Data

Jan. 4, 2000 (NO) .......................................... 20000021

(51) Int. Cl.⁷ .............................. C02F 1/32; C12N 7/00
(52) U.S. Cl. ........................ 210/748; 210/764; 422/24; 422/186.3; 119/226
(58) Field of Search ................................ 210/748, 764, 210/601, 198.1, 205; 422/24, 186.3; 250/432 R, 435, 436; 119/215, 226

(56) References Cited

U.S. PATENT DOCUMENTS

| | | | | | |
|---|---|---|---|---|---|
| 4,467,035 A | * | 8/1984 | Harasawa et al. | .......... | 210/620 |
| 4,752,401 A | * | 6/1988 | Bodenstein | .................. | 210/746 |
| 5,322,569 A | * | 6/1994 | Titus et al. | ..................... | 134/1 |
| 5,413,768 A | * | 5/1995 | Stanley, Jr. | .............. | 422/186.3 |
| 6,086,760 A | * | 7/2000 | Hoffa | .......................... | 210/205 |
| 6,382,134 B1 | * | 5/2002 | Gruenberg et al. | .......... | 119/215 |

FOREIGN PATENT DOCUMENTS

| | | | |
|---|---|---|---|
| JP | 11-098979 A | * | 4/1999 |
| WO | WO 88/01606 | * | 3/1988 |
| WO | WO 98/04124 A1 | * | 2/1998 |

* cited by examiner

Primary Examiner—Frank M. Lawrence
(74) Attorney, Agent, or Firm—Francis C. Hand; Carella, Byrne, Bain et al.

(57) ABSTRACT

A method and a device for the restriction of blooms of micro-organisms in an aqueous system are described. A smaller portion of the body of water in the system is subjected to a radiation treatment, preferably a UV-treatment, whereupon the treated quantity of water is returned to the aqueous system. The UV radiation will induce activation of latent viruses, and when these are returned to the water system, micro-organisms in this system will be killed or inactivated, and new micro-organisms will not be formed.

16 Claims, 1 Drawing Sheet

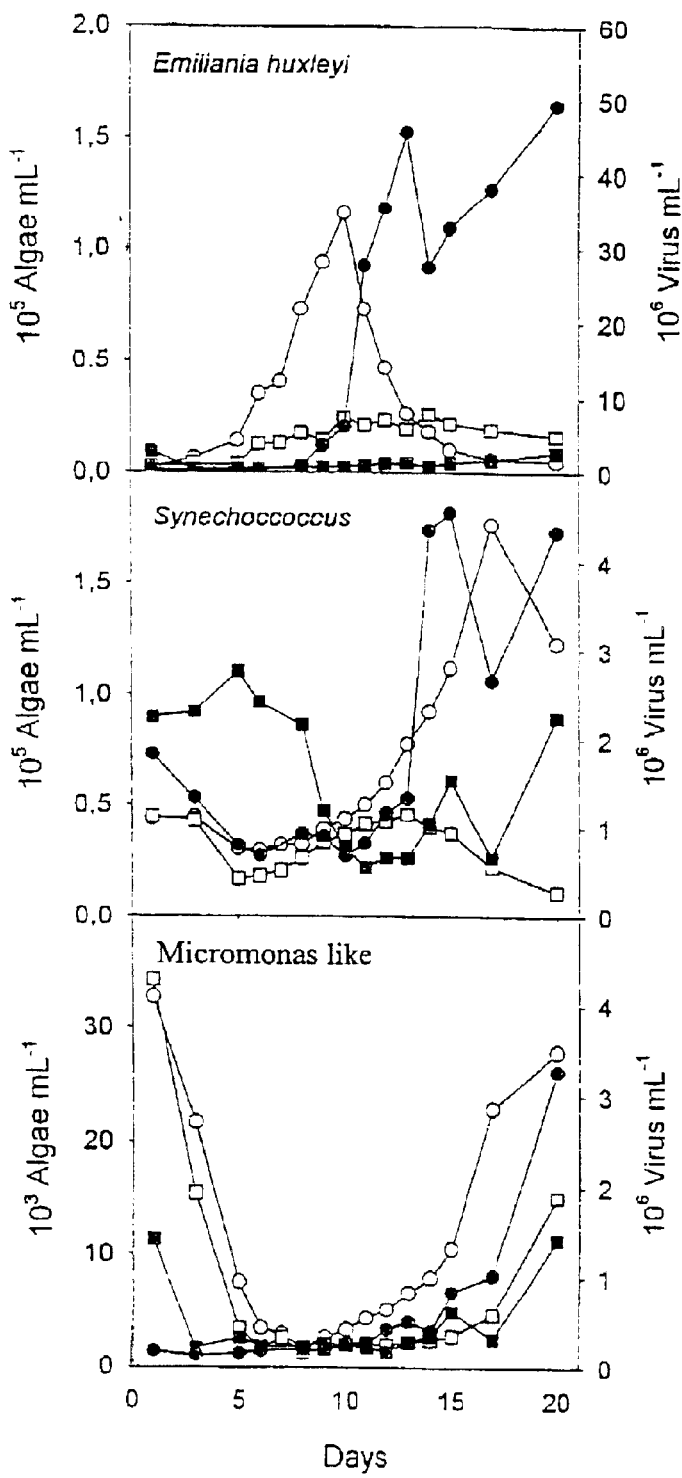
Algae: open symbols
Virus: closed symbols
UV treated: squares
Control: circles

PROCESS AND MEANS TO PREVENT MICROORGANISMS BLOOMING IN AN AQUATIC SYSTEM

The present invention relates to a method and a device for preventing blooms of micro-organisms in an aqueous system, and in particular for preventing blooms of toxin producing micro-algae and cyanobacteria.

In many countries, supply of drinking water is primarily based on the use of surface water, and lakes and rivers which are used as drinking water reservoirs are often vulnerable to blooms of toxin producing micro-algae and cyanobacteria. As a consequence of such blooms, the drinking water sources, which normally supply water of a high quality throughout the year, have had to close temporarily or completely.

Blooms of (micro-)algae also represent considerable ecological and economic problems in marine water systems.

In Norway, such blooms have caused mass deaths of farmed fish, and thus substantial economic losses for the industry. In other parts of the world, such blooms represent a direct threat to the human health situation, at the same time as large stocks of fish are poisoned.

To disinfect drinking water, it is common to treat the water chemically, for example by clorination. It is known that this has many side-effects. The treatment kills the micro-organisms but does not remove toxins which are already in the water. Furthermore, it is known to subject drinking water to UV-treatment in order to activate/kill micro organisms already present.

The principle which is the basis for the present invention is that algae and cyanobacteria are host organisms for viruses, and that an active virus population is often the reason for such algal- and bacterial blooms to culminate naturally.

In the USA and Israel, tests have been carried out in which one has used viruses to restrict blooms of harmful micro-algae. The procedure consists of isolating micro-algae and growing these to produce viruses. Thus, the viruses which are obtained will be specific to the population of algae they were originally collected from, and this specificity is also the likely reason for this procedure not having had the expected effect. In the time it has taken to cultivate the viruses in a monoculture of the algae, other algae will have bloomed. These new populations of algae will not be influenced by the produced viruses, and the effect is reduced or fails to appear.

To establish an effective procedure, the inventors of the present invention have used existing knowledge about UV-induction of viruses to establish a device and a method in which a fraction of a body of water is exposed to UV-treatment to induce virus populations, and in which the UV-treated fraction is thereafter returned to the rest of the water so that the viruses cause a culmination of, or limit the growth of the micro-organisms they are specific to. As the UV-treated fraction is returned to the water reservoir from which it came, and as this occurs immediately after the UV-treatment, the development of virus resistance will not be a problem. Furthermore, viruses will be developed against the different types of algae present in the body of water.

Thus, the present invention comprises a method and a device for treatment of a water system to limit populations of undesirable micro-organisms, or to kill micro-organisms, by inducing an activation of viruses that are latent in the micro-organisms mentioned.

The method according to the present invention is characterised in that a fraction of the aqueous system is subjected to a radiation treatment, and that said fraction is thereafter returned to the aqueous system.

The device, according to the present invention, is characterised in that it comprises a chamber in which a device is arranged to subject the water in the chamber to a radiation with a wavelength in the range 250–380 nm, and means to feed a quantity of water through the chamber.

Generally, it can be assumed that all organisms in nature will be exposed to attack by viruses. However, all viruses are host specific so that they only attack closely related organisms. The specificity is often associated with species, but the viruses can, in some cases, attack related species. The specificity can also be limited to one "strain" within one species.

Viruses occur in nature as free virus particles. These are inactive until they find a host which they can infect and multiply in. Whether a virus particle shall be taken up in a certain host, and whether the virus will be able to multiply in this host, and thereafter separate from the host cells to infect new hosts are based on complex biochemical mechanisms. It is this complex cooperation that makes the host-virus relationship to be very specific.

For algae and bacteria such a virus infection, and subsequent production of virus, will be lethal for the host micro-organisms. In such situations, the host-organisms will develop mechanisms to prevent such attacks, and subsequent virus activity. In higher organisms, the immune system of the organisms will, after some time, provide for identification and destruction of the virus particles. In lower order organisms, the evolution pressure will make the host organisms which develop a resistance (because of genetic multiplicity in such a host population) survive, and thus dominate the population. In this way, resistance to the original virus populations develops over a relatively short time. This leads in turn to the viruses having to be altered so that they again can infect the hosts. Thus, there will continuously be a evolution of both the host organisms and the viruses, and this is one of the reasons the procedure, in which algae are isolated for cultivation of a virus which is returned, does not work, as the time it takes to cultivate the viruses is sufficient for the host organisms to develop resistance, or new populations will have developed.

Furthermore, it is known from many systems (with the human system being one of them) that many organisms are carriers of non-active viruses, i.e. that the virus particles exist latent in the host. In such systems, the virus is under the control of the host so that it does not grow and cause damage. However, if the host is exposed to various kinds of external influences, for example, UV-radiation, then it could possibly lose control over the virus. The virus can then be activated, and it can multiply and can eventually kill the host organism. This will release virus particles which will attack other organisms of the same species.

Therefore, the principle for the invention according to the present application, is to manipulate the host-virus relationship by inducing an activation of the virus populations with the result being that the host organisms are killed, or restricted from growing and multiplying. According to the principle, all effective means which can be shown to lead to an increase in activity of the virus population can be used, but a preferred embodiment of the present invention relates to radiation with light, and especially light having a wavelength within the UV-range.

The following examples describe tests in mesocosmos scale in which the inventors of the present invention have measured the effect of UV-radiation on algae and viruses.

Without being restricted to a specific theory, it is assumed that the causal connection for the measured results is based on the above explanations of induction/activation of virus populations, with the subsequent decreases in algae counts. However, it shall not be excluded that other mechanisms can have had an effect on the measured result, for example, reduced production of toxins etc.

Due to the mentioned specific coupling between a virus and its host organism, there are no health risks associated with use of the procedures according to the present invention. The treatment will only kill or render harmless microorganisms, and will not influence the health of the "end user", be it fish in a marine environment, or people who drink the treated water. For the record, it shall be mentioned that freshwater normally contains between 1–10 million viruses per millilitre.

Seawater also contains normally between 1–10 million viruses per millilitre (Maranger, R. et al., Viral abundance in aquatic systems, a comparison between marine and fresh waters. Mar. Ecol. Prog. Ser., 121, 217–226 (1995)). These virus populations represent an important factor in the regulation of the multitude of species and survival capacity of marine ecosystems. When marine blooms of algae culminate naturally, this will often be associated with the development of virus epidemics (Cannon, R. E., Cyanophage ecology. In: S. M. Goyal, C. P. Gerba and G. Bitten (eds.) Phage Ecology, John Wiley & Sons, New York, pp. 137–1656 (1987); Martin, E. et al. Phages of cyanobacteria. In: R. Calendar (ed), The bacteriophages, Vol 2 Plenum Press, New York, pp. 606–645).

UV-treatment and also combinations of chlorination/UV-treatment of water systems are known. The aim of these procedures is to kill/render harmless already existing microorganisms, and presupposes that the complete body of water must be treated. The procedure according to the present invention is based on a completely different principle, as only a limited fraction (a few percent) of the body of water is subjected to UV-treatment. This induces virus activity, and when this quantity of water is returned to the rest of the water, the increased virus activity will result in the existing micro-organisms being killed, but this will first and foremost have an inhibiting effect on the blooms of new micro-organisms.

The present invention will have large utilitarian value, both nationally and internationally. It will inter alia be of great interest to be able to treat bodies of water to prevent blooms of harmful populations of algae and cyanobacteria. As mentioned, many water works have difficulties in supplying pure drinking water as a consequence of regular annual algae blooms. The acute toxicity of toxins produced by algae has led to many lakes and rivers being no longer suitable as sources of drinking water. The health implications of the use of toxin-containing drinking water are not completely documented, but there are clear indications that such toxins, for example micro-cystein, represent a health risk.

Thus, the present invention could be used as a supplement to, or as a replacement of, existing disinfecting procedures for drinking water.

Furthermore, in recent years, in Norway, as well as in other countries, one has increasingly been confronted by the potentially harmful effects of marine blooms of algae. In Norway, the blooms of algae such as *Prymnesium parvum*, and *Chryschromulina polypepsis* have shown that both fish-farming activities and fisheries are very vulnerable to the effect of harmful algae.

Such blooms of poisonous algae population occur annually as a consequence of draining of nutrient salts from agriculture. The nutrient materials are carried by the rivers to the river mouths, whereupon they move with the prevailing ocean currents, and this can cause damage over large areas. It is uncertain if the treatment of inducing algal viruses will prevent such situations from arising. It will, however, be very decisive that the treatment can be initiated at an early stage, i.e. before the bloom has spread out too much. One visualises a treatment where the blooms at first arise, and otherwise also in areas with limited through-flow of water such as fjords with narrow and shallow outlet areas.

The examples given below shall not be regarded as limiting for the invention as they only explain certain embodiments of the invention. The enclosed claims define the scope and extent of protection.

EXAMPLE 1

UV-Radiation Restricts Blooms of Algae

Two mesocosmoses (large plastic bags (11 $m^3$) which hang in the sea) were filled with seawater, and nitrogen and phosphate were added to initiate blooms of algae. One of the mesocosmos acted as a control. In the other mesocosmos, water from the mesocosmos was pumped through a UV light-source unit of the type UNIK KUV 6–50/1R (UV lamps without reflectors), and thereafter back to the mesocosmos.

The mean velocity of flow through the system was 0.6 $m^3$/hour, and the UV unit gave a minimum dose of 16 $mWs/cm^3$. The UV-treatment lasted for 1 hour for every 24 hours, so that 5% of the total water volume was treated over 24 hours.

The UV-treatment started on day 1, and was terminated on day 17. Samples were taken every day, or every other day for three weeks. Algae and viruses were identified (on the basis of fluorescence and light-scattering characteristics), and counted in a flow-cytometer where the various algae- and virus populations were identified on the basis of the ratio between the signals from "forward" and "side-scatter", combined with counts in a fluorescence microscope.

The results are shown in FIGS 1A–C in which number of algae, *Emiliania huxleyi*, *Synechococcus* and *Micromonas*, and viruses are given for the two mesocosmoses, one in which 5% of the quantity of water (for every 24 hours) is subjected to treatment, the other being the control mesocosmos respectively.

The results show that the blooms of the algae *Emiliania*, *Synechococcus* and *Micromonas* are followed by specific virus populations which increase in number during or after the bloom. This is interpreted as the algae being subjected to attacks by viruses in nature, and that the viruses influence the population dynamics of the algae.

By UV-treatment of a fraction of the body of water, there was no noticeable blooms of algae. This is interpreted as the induction of the viruses killing existing algae, and/or preventing blooms of new algae. However, the virus numbers are also lower than in the control, even if virus activity is induced, and a probable explanation for this is fewer algae. The amount ratio (number of viruses in relation to number of algae) is higher in the UV-treatment than in the control, apart from when the blooms of Emiliania collapsed naturally in the control test. This indicates that the fraction of algal cells that produce virus, i.e. algae which are induced or infected, are higher in this mesocosmos than in the control so that net production of algae here is lower, with the consequence being that the blooms are avoided.

The results show clearly that if a smaller quantity of water (for example 5% per 24 hours) is subjected to UV-treatment, this will prevent blooms of algae.

What is claimed is:

1. A method of treating an aqueous system comprising the steps of removing a fraction of the aqueous system;

subjecting the removed fraction to radiation in an amount sufficient to activate a latent virus in the removed fraction; and thereafter returning the radiated fraction to the aqueous system to inhibit growth of microorganisms which act as host organisms for said virus in the aqueous system.

2. A method as set forth in claim 1 wherein said radiation has a wave length in the UV range of 250 to 350 nm.

3. A method as set forth in claim 1 wherein said fraction is less than 20% of the aqueous system during a 24 hour period.

4. A method as set forth in claim 1 wherein said fraction is from 1 to 10% of the aqueous system during a 24 hour period.

5. A method as set forth in claim 3 wherein said fraction is about 5% of the aqueous system during a 24 hour period.

6. A method as set forth in claim 1 wherein the treatment of said fraction is pulsed and sufficient for activation of a latent virus in said fraction.

7. A method as set forth in claim 1 wherein the treatment of said fraction is continuous and sufficient for activation of a latent virus in said fraction.

8. A method as set forth in claim 1 wherein the aqueous system is a source of drinking water.

9. A method as set forth in claim 1 wherein the aqueous system is a marine system.

10. A method as set forth in claim 1 wherein said microorganisms act as host organisms for said latent virus and wherein said latent virus is induced and activated by said radiation.

11. A method as set forth in claim 1 wherein said microorganisms are eukaryotes including algae and protozoae.

12. A method as set forth in claim 1 wherein said microorganisms are prokaryotes.

13. A system for restricting a bloom of micro-organisms in an aqueous system, said system comprising a chamber for receiving a flow of water;

means in said chamber for subjecting the flow of water to radiation in a range of from 250 to 380 nm and in an amount sufficient to activate a latent virus in the flow of water; and means for returning the flow of water to an aqueous system to inhibit growth of microorganisms which act as host organisms for said virus in the aqueous system.

14. A system as set forth in claim 13 wherein said means in said chamber includes an adjustable wavelength regulator for setting a predetermined wavelength.

15. A system as set forth in claim 13 further comprising means for regulating a flow of water through said chamber.

16. A system as set forth in claim 13 further comprising means for regulating the radiation effect.

* * * * *